US00RE48665E

(19) United States
(12) Reissued Patent
Jensen et al.

(10) Patent Number: US RE48,665 E
(45) Date of Reissued Patent: Aug. 3, 2021

(54) METHOD OF ISOLATING NUCLEIC ACID FROM SPECIMENS IN LIQUID-BASED CYTOLOGY PRESERVATIVES CONTAINING FORMALDEHYDE

(71) Applicant: GEN-PROBE INCORPORATED, San Diego, CA (US)

(72) Inventors: Deborah C. Jensen, San Diego, CA (US); Brett W. Kirkconnell, San Diego, CA (US); Timothy J. Wilson, San Diego, CA (US)

(73) Assignee: GEN-PROBE INCORPORATED, San Diego, CA (US)

(21) Appl. No.: 16/548,790

(22) Filed: Aug. 22, 2019

Related U.S. Patent Documents

Reissue of:
(64) Patent No.: 9,771,572
Issued: Sep. 26, 2017
Appl. No.: 15/121,907
PCT Filed: Mar. 21, 2014
PCT No.: PCT/US2014/000064
§ 371 (c)(1),
(2) Date: Aug. 26, 2016
PCT Pub. No.: WO2015/130255
PCT Pub. Date: Sep. 3, 2015

U.S. Applications:
(60) Provisional application No. 61/946,367, filed on Feb. 28, 2014.

(51) Int. Cl.
*C12Q 1/68* (2018.01)
*C12N 15/10* (2006.01)

(52) U.S. Cl.
CPC ..... *C12N 15/1003* (2013.01)

(58) Field of Classification Search
CPC ..... C12N 15/1003
See application file for complete search history.

(56) References Cited

U.S. PATENT DOCUMENTS

| | | | | |
|---|---|---|---|---|
| 5,665,546 | A * | 9/1997 | Cubbage | C12Q 1/6841 435/5 |
| 6,380,353 | B1 * | 4/2002 | Rupaner | C07B 63/04 524/555 |
| 8,236,263 | B2 | 8/2012 | Green et al. | |
| 8,303,872 | B2 | 11/2012 | Szafranski et al. | |
| 8,986,947 | B2 | 3/2015 | Boren et al. | |
| 9,574,225 | B2 | 2/2017 | Himmelreich et al. | |
| 2006/0008807 | A1 * | 1/2006 | O'Hara | C12N 1/06 435/6.14 |
| 2007/0042355 | A1 | 2/2007 | Adelson et al. | |
| 2009/0082245 | A1 | 3/2009 | Smith et al. | |
| 2009/0202998 | A1 | 8/2009 | Schlumpberger et al. | |
| 2010/0261015 | A1 * | 10/2010 | Szafranski | C07D 233/34 428/402 |
| 2011/0196146 | A1 | 8/2011 | Khripin et al. | |
| 2011/0209538 | A1 | 9/2011 | Zhang | |
| 2011/0256530 | A1 * | 10/2011 | Hogan | G01N 1/30 435/6.1 |
| 2012/0196274 | A1 | 8/2012 | Rangwala et al. | |
| 2013/0280728 | A1 * | 10/2013 | Schlumpberger | C12N 15/1003 435/6.12 |

FOREIGN PATENT DOCUMENTS

| | | | |
|---|---|---|---|
| DE | 19814873 | A1 | 10/1999 |
| DE | 10200713368 | A1 | 9/2008 |
| EP | 2458015 | A1 | 5/2012 |
| WO | 94/07532 | A1 | 4/1994 |
| WO | 03/035895 | A2 | 5/2003 |
| WO | 2005054466 | A2 | 6/2005 |
| WO | 2007068764 | A1 | 6/2007 |
| WO | 2008012104 | A2 | 1/2008 |
| WO | 2008119488 | A1 | 10/2008 |
| WO | 2009002937 | A2 | 12/2008 |
| WO | 2009080513 | A1 | 7/2009 |
| WO | 2010054467 | A1 | 5/2010 |
| WO | 2010072822 | A2 | 7/2010 |
| WO | 2011032124 | A1 | 3/2011 |
| WO | 2011082415 | A2 | 7/2011 |
| WO | 2011094528 | A2 | 8/2011 |
| WO | 2011104027 | A1 | 9/2011 |

OTHER PUBLICATIONS

N. Masuda et al. Analysis of chemical modification of RNA from formalin-fixed samples and optimization of molecular biology applications for such samples. Nucleic Acids Research, 27(22): 4436-4443, 1999.*

Wikipedia, Imidazolidinyl urea, available at https://en.wikipedia.org/wiki/Imidazolidinyl_urea, attached, accessed Apr. 28, 2017.*

NIST, 2-Imidazolidinone, available at http://webbook.nist.gov/cgi/cbook.cgi?ID=120-93-4, attached, accessed Apr. 28, 2017.*

Analytical Evaluation of APTIMA HPV Assay Performance with SurePath Liquid-Based Cytology Specimens Using an Improved Specimen Treatment Method, Hologic Gen-Probe, San Diego, CA.

PanReac AppliChem GmbH, ITW Reagents, Spezifikation, Proteinase K-A3830, Seite 3 von 1-3 (www.applichem.com).

Ambion by Life Technologies, Proteinase K Solution, Catalog No. AM2546, AM2548, Pub. No. 4393871, Rev. C.

Textile Chemicals, K. Lacasse & W. Baumann, Environmental Data and Facts, Springer.

ROMPP Lexikon, Chemie, Cm-G, George Thieme Verlag, Stuttgart, New York.

ROMPP Lexikon, Chemie, T-Z, George Thieme Verlag, Stuttgart, New York.

Notice of Opposition to German Patent No. DE 10 2015 203 606 by QIAGEN GmbH, Feb. 20, 2017.

(Continued)

*Primary Examiner* — Bruce R Campell
(74) *Attorney, Agent, or Firm* — Finnegan, Henderson, Farabow, Garrett & Dunner LLP

(57) ABSTRACT

Method, composition, kit and system for isolating amplifiable nucleic acid from specimens preserved in a liquid-based cytology preservative that contains formaldehyde. The technique relies on the use of 2-imidazolidone and a protease enzyme, such as proteinase K, at elevated temperatures. Advantageously, RNA can be isolated and used as a template in nucleic acid amplification reactions.

39 Claims, 9 Drawing Sheets

(56) References Cited

OTHER PUBLICATIONS

Masuda, N. et al., "Analysis of chemical modification of RNA from formalin-fixed samples and optimization of molecular biology applications for such samples," Nucleic Acid Res., 1999, 12(27):4436-43, London, Information Retrieval ltd.
Loudig, O. et al., "Molecular restoration of archived transcriptional profiles by complementary-template reverse-transcription (CT-RT)," Nucleic Acid Res., 2007, 35(15):1-14, e94, London, Information Retrieval ltd.
Data sheet on TRIzol Reagent, obtainable from www.thermofisher.com/order/catalog/product/1559602.
Wikipedia entry concerning, Dimethylol ethylene urea.
DPMA, Office Action, German Patent Application No. 10 2015 017 080.5, Dec. 14, 2016.
Niehaus et al., "Enzymes for the Laundry Industries: Tapping the Vast Metagenomic Pool of Alkaline Proteases," Microb Biotechnol. 2011, (6):767-76.
USPTO Notice of Allowance, U.S. Appl. No. 14/635,955, Jun. 29, 2017.
UKIPO, Examination Report, United Kingdom Application No. GB1503297.2, Jun. 7, 2017.
Kawashima et al., "Efficient extraction of proteins from formalin-fixed paraffin-embedded tissues requires higher aoncentration of tris(hydroxymethyl)aminomethane," Clinical Proteomics, 2014, 11:4, Bio Med Central Ltd., UK.
Klopfleisch et al., "Excavation of a buried treausure—DNA, mRNA, miRNA and protein analysis in formalin fixed, paratin embedded tissues," Hitol Histopathol, 2011, 26:797-810, Spain.
ethylene-urea-XP002771174 (Abstract).
EPO European Extended Search Report, European Patent Application No. 14883689.3, Jul. 18, 2017.
UPO Official Action, Japanese Patent Application No. 2016-554363, Jul. 12, 2017.
USPTO Notice of Allowance, U.S. Appl. No. 14/635,955, Aug. 1, 2017.

* cited by examiner

METHOD OF ISOLATING NUCLEIC ACID FROM SPECIMENS IN LIQUID-BASED CYTOLOGY PRESERVATIVES CONTAINING FORMALDEHYDE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATION

The present application is a National Stage entry from PCT application PCT/US2014/000064, filed Mar. 21, 2014, which claims the benefit under 35 U.S.C. § 119(e) of non-provisional of 61/946,367 filed Feb. 28, 2014, which is incorporated by reference in its entirety for all purposes.

FIELD OF THE INVENTION

The present invention relates to the field of biotechnology. More particularly, the invention relates to methods of isolating nucleic acid from samples fixed in a formaldehyde-containing liquid-based cytology preservative, where isolated RNA is suitable for use as a template in nucleic acid amplification procedures.

BACKGROUND OF THE INVENTION

Laboratory personnel engaged in molecular analysis of nucleic acid isolated from formaldehyde-fixed samples appreciate that certain restrictions apply to the use of this sample type. This is because formaldehyde, and certain other chemical fixatives, chemically modify proteins and nucleic acids. These modifications are known to compromise the utility of nucleic acid in subsequent analyses.

Particular difficulties result from the well-known chemical modification of DNA, RNA and proteins. Indeed, Masuda et al., (Nucleic Acids Res., 27:4436-4443 (1999)) investigated the reason formalin-fixed samples are poor materials for molecular biological applications. The authors demonstrated that, while treatment with proteinase K solubilized fixed tissues and enabled RNA extraction, the extracted RNA was of only limited use as a PCR template. Further investigation revealed chemical addition of monomethylol groups (—$CH_2OH$) to all four bases, as well as evidence for adenine dimerization through methylene bridging. Certain modifications could be reversed by elevating the temperature in formalin-free buffer. However, the instability of RNA can make the use of high temperature conditions undesirable.

Earlier approaches for treating formaldehyde-fixed samples have met with some success. For example, Khripin et al., in published U.S. Patent Application 2011/0196146 A1 described the use of hydrazine- and hydrazide-containing formaldehyde-scavenging compounds during isolation of nucleic acids from cellular material disposed in a liquid-based cytology preservative containing formaldehyde (e.g., semicarbazide; thiosemicarbazide; carbazide; thiocarbazide; N-aminoguanidine and a salt thereof, including hydrochloride salts; N,N-diaminoguanidine and a salt thereof, including dihydrochloride salts; acetylhydrazide; adipic acid dihydrazide; succinic acid dihydrazide; formic hydrazide; maleic acid dihydrazide; malonic acid dihydrazide; benzenesulfonylhydrazide; tosylhydrazide; methylsulfonylhydrazide). Rather than employing nucleic acid amplification as a measure of nucleic acid integrity, the inventors employed a hybrid capture protocol wherein a cocktail of RNA probes hybridized to isolated nucleic acid. This was followed by antibody binding to the RNA:DNA hybrids, and a subsequent signal amplification procedure to determine the presence of DNA target nucleic acids. Indeed, Khripin et al., refer to U.S. Pat. No. 6,228,578 for instructing nucleic acid detection, where that reference describes treatment of nucleic acid samples under conditions of strong alkali and high temperature—conditions known to hydrolyze RNA. Thus, Khripin et al., do not address rendering nucleic acids suitable for use as templates in nucleic acid amplification reactions, nor present sufficient disclosure to allow detection of RNA targets from formaldehyde-fixed specimens.

The techniques disclosed herein address the need for rapid and efficient isolation of intact nucleic acid, such as RNA, from specimens preserved in formaldehyde-containing liquid-based cytology preservatives.

SUMMARY OF THE CLAIMED INVENTION

In one aspect, the invention relates to a method of processing a specimen that includes a clinical sample disposed in a liquid-based cytology preservative that contains formaldehyde. The method begins with the step of combining the specimen with a protease enzyme and 2-imidazolidone or other formaldehyde scavenger to create a reaction mixture. This is followed by incubating the reaction mixture at an elevated temperature for a period of time sufficient to reverse chemical modifications by formaldehyde of nucleic acid that may be contained in the specimen. By this step, at least some of the chemical modifications caused by reaction between formaldehyde and either nucleic acids or proteins are reversed. For example, chemical crosslinks may be broken. Next there is a step for isolating a nucleic acid from the reaction mixture after the incubating step. Finally, there is a step for performing an in vitro amplification reaction using the nucleic acid from the isolating step as templates.

In some methods, the reversing releases nucleic acids in the specimen from formaldehyde-induced crosslinking to polypeptides in the specimen. In some methods, the protease frees the nucleic acids from the formaldehyde-induced crosslinking and 2-imidazolidone inhibits induction of new cross-links between nucleic acids and polypeptides in the sample.

In some methods, the sample has been disposed in the liquid-based cytology preservative for 7-120 days before performing step (a).

In some methods, the incubating step is for no more than 30 minutes or the incubating step is between about 5 minutes and 30 minutes or the incubating step is for no more than 15 min.

In some methods, the yield of amplified nucleic acid after step (d) is higher than in control amplifications omitting either the proteinase or 2-imidazolidone. In some methods, the yield of amplified nucleic acid after step (d) is at least 10% higher than either of control amplifications omitting either proteinase or 2-imidazolidone. In some methods, at least 90% of the nucleic acid molecules in the sample are free of the cross-links after the incubating step.

In some methods, final concentration of 2-imidazolidone before the incubation step is 1 to 5 or 2-5 fold by moles greater than final maximum concentration of the formaldehyde. In some methods, the proteinase is proteinase-K present at a concentration of 4.3 to 43 U/ml. In some methods, the temperature of the incubating step is about 60-100° C. In some methods, the temperature of the incubating step is 85-95° C. In some methods, the temperature of the incubating step is 91-95° C. In some methods, the temperature of the incubating step is 90° C.

In some methods, the proteinase and formaldehyde scavenger are combined simultaneously with the specimen. In some methods, the proteinase is combined with the specimen before formaldehyde scavenger. In some methods, the formaldehyde scavenger is combined with the specimen before the proteinase.

In some methods, the amplification is a transcription mediated amplification, single-primer nucleic acid amplification, nucleic acid sequence-based amplification, polymerase chain Reaction, strand displacement amplification, self-sustained sequence replication or DNA ligase chain reaction. In some methods, the nucleic acids comprise DNA and in some methods RNA. In some methods, the isolated nucleic acid is DNA and in some methods RNA.

In some methods, the nucleic acid is isolated by a capture assay with a capture probe hybridizing to the nucleic acid to be isolated and to an immobilized probe. In some methods, the immobilized probe is immobilized to a magnetic bead.

In some methods, the assay positivity of amplified nucleic acid is higher than assay positivity of amplified nucleic acids obtained from reaction mixture omitting either proteinase or the formaldehyde scavenger. In some methods, the assay positivity of amplified nucleic acid is at least about 12% higher than assay positivity of amplified nucleic acids obtained from reaction mixture omitting either proteinase or 2-imidazolidone. In some methods, the assay positivity of amplified nucleic acid after step (d) is about 95% after 21 days.

In some methods, the isolated nucleic acid is human papillomavirus (HPV) RNA target nucleic acid. In some methods, the specimen is a cervical cell specimen.

In another aspect, the invention relates to a composition of matter that includes the following components: 2-imidazolidone; proteinase K; EDTA; and a pH buffer.

In another aspect, the invention relates to a kit for processing a specimen preserved in a liquid-based cytology preservative that contains formaldehyde. The kit includes a first vial containing a lyophilized proteinase K enzyme. As well, the kit includes a second vial containing a reconstitution buffer for reconstituting the lyophilized proteinase K enzyme. This reconstitution buffer includes an amount of a pH buffer, an amount of EDTA, and an amount of 2-imidazolidone.

In another aspect, the invention relates to a system for processing nucleic acid-containing samples preserved in a liquid-based cytology preservative that contains formaldehyde. The system components include: a programmable controller; a pipetting device in communication with the programmable controller; a first holder for a reaction vial; and a second holder for a reagent vial. In accordance with this aspect of the invention, the programmable controller is configured by software instructions to cause the pipetting device to transfer an aliquot of liquid from the reagent vial to the reaction vial when the reagent vial contains a solution comprising 2-imidazolidone, proteinase K, EDTA, and a pH buffer. As well as these components, the reaction vial can contain a specimen preserved in formaldehyde as further described below introduced before or after the other components. The same or other pipetting device can be used for introducing the specimen into the reaction vial, optionally with the programmable controller being configured by software to cause such pipetting device to operate. The system can also include a heater for heating the reaction vial and its contents for a controlled period of time, optionally subject to the control of the programmable controller configure by suitable software.

BRIEF DESCRIPTION OF THE DRAWINGS

FIG. 2A shows results obtained using SiHa cells that contained HPV 16. FIG. 2B shows results obtained using HeLa cells that contained HPV 18. FIG. 2C shows results obtained using MS751 cells that contained HPV 45. In each of FIGS. 2A-2C, open bars indicate % positivity (left scale), and thick horizontal lines indicate average signal/cutoff ratio (right scale).

FIG. 3A presents results obtained using SiHa cells. FIG. 3B presents results obtained using HeLa cells. The different lines indicate treatment with proteinase K alone (▩); and with the combination of 2-imidazolidone and proteinase K (♦).

DEFINITIONS

Figure 1:
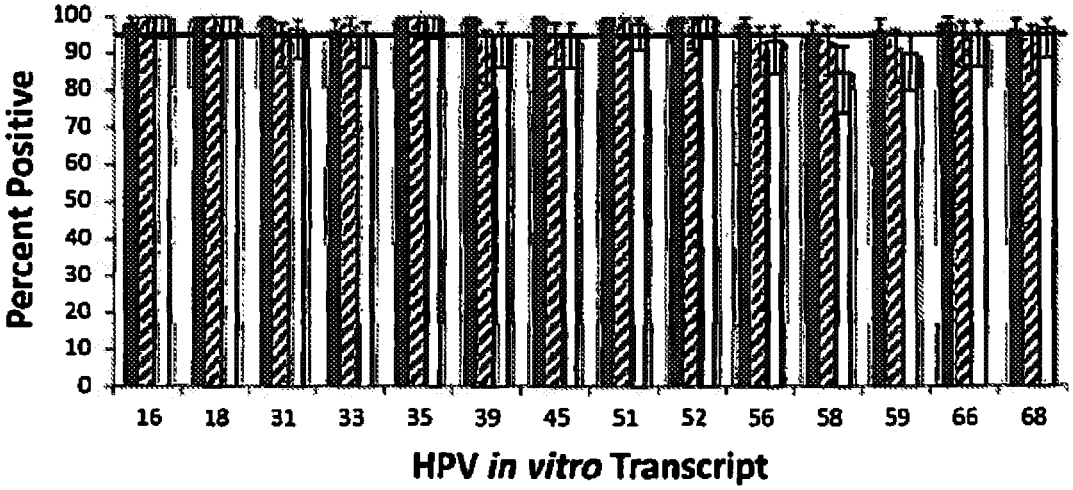
FIG. 1 is a bar graph showing % positivity in the HPV RNA amplification and detection assay performed using in vitro transcripts. Three conditions used in the procedure were: (1) specimens preserved in THINPREP liquid-based cytology preservative (solid fill); (2) specimens preserved in SUREPATH liquid-based cytology preservative and treated with proteinase K enzyme (diagonal fill); and (3) specimens preserved in SUREPATH liquid-based cytology preservative and treated with the combination of 2-imidazolidone and proteinase K enzyme at elevated temperature (open bars).

Unless otherwise described, scientific and technical terms used herein have the same meaning as commonly understood by those skilled in the art of molecular biology based on technical literature, e.g., Dictionary of Microbiology and Molecular Biology, 2nd ed. (Singleton et al., 1994, John Wiley & Sons, New York, N.Y.), or other well-known technical publications related to molecular biology. Unless otherwise described, techniques employed or contemplated herein are standard methods well known in the art of molecular biology.

All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

Approximating language, as used herein throughout the specification and claims, may be applied to modify any quantitative or qualitative representation that could permissibly vary without resulting in a change in the basic function to which it is related. Accordingly, a value modified by a term such as "about" or "approximately" is not to be limited to the precise value specified, and may include values that differ from the specified value.

For clarification, "formaldehyde," in its basic form ($CH_2O$), is a gas. The liquid called "formalin" is actually a mixture of formaldehyde gas and water. However, as used herein, "formaldehyde" can refer to the molecule ($CH_2O$) that is dissolved in an aqueous solution.

As used herein, "liquid-based cytology" refers to liquid-based gynecologic specimen collection, wherein a sample for cervicovaginal testing collected in the conventional manner with one of the brush instruments but, instead of being spread onto a glass slide, it is transferred to a vial of liquid preservative or "fixative." The preserved specimen can be used for microscopy or molecular analysis.

As used herein, a "specimen" is something collected as an example of a particular kind of thing. Biological specimens include any tissue or material derived from a living or dead organism that may contain an analyte, such as a nucleic acid analyte. Preferred biological specimens include respiratory tissue, exudates (e.g., bronchoalveolar lavage), biopsy, sputum, peripheral blood, plasma, serum, lymph node, gastrointestinal tissue, feces, urine, or other fluids, tissues or materials. Highly preferred biological specimens include cells collected from the outer opening of the cervix, as may be obtained in connection with PAP testing.

As used herein, the term "sample" refers to a portion or quantity of material for use in testing, where that portion can be informative about the thing from which it was taken. Samples may be from any source, such as biological specimens or environmental sources.

As used herein, the term "nucleic acid" refers to a polynucleotide compound, which includes oligonucleotides, comprising nucleosides or nucleoside analogs that have nitrogenous heterocyclic bases or base analogs, covalently linked by standard phosphodiester bonds or other linkages. Nucleic acids include RNA, DNA, chimeric DNA-RNA polymers or analogs thereof.

By "analyte nucleic acid" is meant a polynucleotide of interest that is to be detected or quantified. The genome of a particular virus would exemplify an analyte nucleic acid.

As used herein, a "test sample" is any sample to be investigated for the presence of a particular analyte nucleic acid.

As used herein, "elevated" temperature conditions refer to a temperature higher than room temperature. Preferably, elevated temperatures are in the range of from 60° C.-100° C., more preferably in the range of from 65° C.-95° C., sometimes in the range of from 80° C.-90° C., sometimes 81-98° C., 85-98° C., 85-95° C., 90-95° C., 91-95° C. or 91-99° C., and sometimes about 90° C. Use of temperatures above 80° C., e.g., 85-98° C., 90° C., or 91-95° C. can result in increased assay sensitivity as further defined below, which is surprising because proteinase K undergo increasing denaturation as the temperature is increased over 65° C., and would not normally be recommended for use at temperatures above 85° C. or 90° C. because of excessive denaturation. Although practice of the invention is not dependent on discerning the mechanism for this unexpected benefit from higher temperatures, this result may indicate that promotion of 2-imidazolidone scavenging of formaldehyde at the elevated temperature more than compensates for some reduction in proteinase K activity. Preferably, in all of these instances, reaction mixtures including a clinical sample in liquid-based cytology preservative, 2-imidazolidone, protease, EDTA and pH buffer are exposed to elevated temperatures for a period of time from 10 minutes to 30 minutes, and preferably from 10 minutes to not more than 20 minutes, and sometimes for up to 15 minutes or about 15 minutes.

An "amplicon" is a polynucleotide product of an in vitro nucleic acid amplification reaction, wherein a target nucleic acid sequence served as the template for synthesis of copies or amplification products.

By "target" or "target nucleic acid" is meant a nucleic acid containing a sequence that is to be amplified, detected and/or quantified. A target nucleic acid sequence that is to be amplified preferably are positioned between two oppositely disposed oligonucleotides, and includes the portion of the target nucleic acid that is complementary to each of the oligonucleotides.

By "amplification" or "nucleic acid amplification" or "in vitro nucleic acid amplification" and the like is meant any known procedure for obtaining multiple copies, allowing for RNA and DNA equivalents, of a target nucleic acid sequence or its complement or fragments thereof.

To aid in understanding of some of the embodiments disclosed herein, the TMA method that has been described in detail previously (e.g., U.S. Pat. Nos. 5,399,491, 5,554,516 and 5,824,518) is briefly summarized. In TMA, a target nucleic acid that contains the sequence to be amplified is provided as single stranded nucleic acid (e.g., ssRNA or ssDNA). Any conventional method of converting a double stranded nucleic acid (e.g., dsDNA) to a single-stranded nucleic acid may be used. A promoter primer binds specifically to the target nucleic acid at its target sequence and a reverse transcriptase (RT) extends the 3' end of the promoter primer using the target strand as a template to create a cDNA copy, resulting in a RNA:cDNA duplex. RNase activity (e.g., RNase H of RT enzyme) digests the RNA of the RNA:cDNA duplex and a second primer binds specifically to its target sequence in the cDNA, downstream from the promoter-primer end. Then RT synthesizes a new DNA strand by extending the 3' end of the second primer using the cDNA as a template to create a dsDNA that contains a functional promoter sequence. RNA polymerase specific for the functional promoter initiates transcription to produce about 100 to 1000 RNA transcripts (amplified copies or amplicons) complementary to the initial target strand. The second primer binds specifically to its target sequence in each amplicon and RT creates a cDNA from the amplicon RNA template to produce a RNA:cDNA duplex. RNase digests the amplicon RNA from the RNA:cDNA duplex and the target-specific sequence of the promoter primer binds to its complementary sequence in the newly synthesized DNA and RT extends the 3' end of the promoter primer as well as the 3' end of the cDNA to create a dsDNA that contains a functional promoter to which the RNA polymerase binds and transcribes additional amplicons that are complementary to the target strand. Autocatalytic cycles that use these steps repeatedly during the reaction produce about a billion-fold amplification of the initial target sequence. Amplicons may be detected during amplification (real-time detection) or at an end point of the reaction (end-point detection) by using a probe that binds specifically to a sequence contained in the amplicons. Detection of a signal resulting from the bound probes indicates the presence of the target nucleic acid in the sample.

As used herein, "detection" of the amplified products may be accomplished by using any known method. For example, the amplified nucleic acids may be associated with a surface that results in a detectable physical change (e.g., an electrical change). Amplified nucleic acids may be detected in solution phase or by concentrating them in or on a matrix and detecting labels associated with them (e.g., an intercalating agent such as ethidium bromide). Other detection methods use probes complementary to a sequence in the amplified product and detect the presence of the probe:product complex, or use a complex of probes to amplify the signal detected from amplified products (e.g., U.S. Pat. Nos. 5,424,413, 5,451,503 and 5,849,481). Other detection methods use a probe in which signal production is linked to the presence of the target sequence because a change in signal results only when the labeled probe binds to amplified product, such as in a molecular beacon, molecular torch, or hybridization switch probe (e.g., U.S. Pat. Nos. 5,118,801, 5,312,728, 5,925,517, 6,150,097, 6,361,945, 6,534,274, 6,835,542, 6,849,412 and 8,034,554; and U.S. Pub. No. 2006/0194240 A1). Such probes typically use a label (e.g., fluorophore) attached to one end of the probe and an interacting compound (e.g., quencher) attached to another location of the probe to inhibit signal production from the label when the probe is in one conformation ("closed") that indicates it is not hybridized to amplified product, but a detectable signal is produced when the probe is hybridized to the amplified product which changes its conformation (to "open"). Detection of a signal from directly or indirectly labeled probes that specifically associate with the amplified product indicates the presence of the target nucleic acid that was amplified.

As used herein, a "probe" is an oligonucleotide that hybridizes specifically to a target sequence in a nucleic acid, preferably in an amplified nucleic acid, under conditions that promote hybridization, to form a detectable hybrid.

As used herein, the term "contacting" means bringing two or more components together. Contacting can be achieved by mixing all the components in a fluid or semi-fluid mixture. Contacting can also be achieved when one or more components are brought into physical contact with one or more other components on a solid surface such as a solid tissue section or a substrate.

As used herein, the term "target capture" refers to selectively separating a target nucleic acid from other components of a sample mixture, such as cellular fragments, organelles, proteins, lipids, carbohydrates, or other nucleic acids. A target capture system may be specific and selectively separate a predetermined target nucleic acid from other sample components (e.g., by using a nucleic acid sequence specific to the intended target nucleic acid), or it may be nonspecific and selectively separate a target nucleic acid from other sample components by using other characteristics of the target (e.g., a physical trait of the target nucleic acid that distinguishes it from other sample components which do not exhibit that physical characteristic, such as hybridization to a non-specific nucleic acid, binding to a porous glass bead, capture and elution in a silica packed column). Preferred nucleic acid hybridization target capture methods and compositions have been previously described in detail (U.S. Pat. Nos. 5,750,338, 6,060,246, 6,110,678, 6,534,273 and 7,993,853; and US Pub. No. 2008/0286775 A1). Preferred target capture embodiments use a target capture oligonucleotide in solution phase and an immobilized capture probe attached to a support to form a complex with the target nucleic acid and separate the captured target from other components.

As used herein, the term "target capture oligonucleotide" refers to at least one nucleic acid oligonucleotide that bridges or joins a target nucleic acid and an immobilized capture probe by using binding pair members, such as complementary nucleic acid sequences or biotin and streptavidin. In one approach, the target capture oligonucleotide binds nonspecifically to the target nucleic acid and immobilizes it to a solid support. In a different approach, a target specific (TS) sequence of the target capture oligonucleotide binds specifically to a sequence in the target nucleic acid. In both approaches the target capture oligonucleotide includes an immobilized capture probe-binding region that binds to an immobilized capture probe (e.g., by specific binding pair interaction). In embodiments in which the TS sequence and the immobilized capture probe-binding region are both nucleic acid sequences, they may be covalently joined to each other, or may be on different oligonucleotides joined by one or more linkers.

An "immobilized capture probe" provides a means for joining a target capture oligonucleotide to a solid support. The immobilized capture probe is a base sequence recognition molecule joined to the solid support, which facilitates separation of bound target polynucleotide from unbound material. Any known solid support may be used, such as matrices and particles free in solution. For example, solid supports may be nitrocellulose, nylon, glass, polyacrylate, mixed polymers, polystyrene, silane polypropylene and, preferably, magnetically attractable particles. Particularly preferred supports include magnetic spheres that are monodisperse (i.e., uniform in size ± about 5%), thereby providing consistent results, which is particularly advantageous for use in an automated assay. The immobilized capture probe may be joined directly (e.g., via a covalent linkage or ionic interaction), or indirectly to the solid support. Common examples of useful solid supports include magnetic particles or beads.

As used herein, the term "separating" or "purifying" generally refers to removal of one or more components of a mixture, such as a sample, from one or more other components in the mixture. Sample components include nucleic acids in a generally aqueous solution phase, which may include cellular fragments, proteins, carbohydrates, lipids, and other compounds. Preferred embodiments separate or remove at least 70% to 80%, and more preferably about 95%, of the target nucleic acid from other components in the mixture.

By "kit" is meant a packaged combination of materials, typically intended for use in conjunction with each other. Kits in accordance with the invention may include instructions or other information in a "tangible" form (e.g., printed information, electronically recorded on a computer-readable medium, or otherwise recorded on a machine-readable medium such as a bar code for storing numerical values).

By "consisting essentially of" is meant that additional component(s), composition(s) or method step(s) that do not materially change the basic and novel characteristics of the present invention may be included in the present invention. Any component(s), composition(s), or method step(s) that have a material effect on the basic and novel characteristics of the present invention would fall outside of this term.

Unless otherwise apparent from the context, "about" indicates variations implicit in the accuracy with which a value can be measured.

"Reversing" modifications of DNA refers to freeing DNA from modifications induced by formaldehyde, particularly cross-links to polypeptides. Reversing may be partial or complete and may or may not result in restoration of DNA to its precise state before formaldehyde-induced modifications occurred.

DETAILED DESCRIPTION

Disclosed herein are methods, systems, compositions and kits for isolating nucleic acid from specimens preserved in liquid-based cytology preservatives containing formaldehyde. Briefly, the disclosed approach relies on contacting an aliquot of the sample, meaning the cellular sample disposed in the liquid preservative, with a combination of 2-imidazolidone and a protease enzyme. In a highly preferred embodiment, the protease is the proteinase K enzyme. The mixture can then be incubated under conditions of high heat to inactivate free formaldehyde and reverse at least a portion of the chemical modifications of nucleic acid caused by formaldehyde. The approach advantageously is rapid compared to prior methods, and results in nucleic acid, including RNA, that can be efficiently isolated (e.g., by capture probe hybridization), reverse transcribed (if desired) and amplified in vitro.

Introduction and Overview

The techniques disclosed herein facilitate detection of nucleic acid targets that may be present in biological samples contained in liquid-based cytology preservatives that include formaldehyde. Such biological samples can be stored for substantial periods before undergoing analysis (e.g., at least 1, 2, 7, 14, 30, 50 or 100 days, or 7-120 days). During storage, formaldehyde can induce modifications of the nucleic acids in the sample, particularly generation of cross-links with polypeptides present in the sample. These modification inhibit subsequent processing of the DNA including its ability to hybridize (e.g., to a capture probe), or be amplified. Modifications, including cross-links can be broken by a treatment with a protease, such as proteinase K. Treatment with a protease can increase the molecules of nucleic acid available for capture and/or amplification and ultimately yield more amplification product and/or a lower threshold of detection of a particular target. These beneficial effects of protease are increased by concurrent treatment of the sample with 2-imidazolidone. The 2-imidazolidone acts as a formaldehyde scavenger, i.e., it reacts with formaldehyde in such a way as to render it incapable or at least of substantially diminished ability to induce crosslinks between nucleic acids and polypeptides. Although 2-imidazolidone is used as an exemplary and preferred formaldehyde scavenger in much of the description that follows, other formaldehyde scavengers, such as those described in the Background can alternatively be used, and particularly so in embodiments performed at a temperature of 85° C. or higher unless the context requires otherwise. By removing reactive formaldehyde, the 2-imidazolidone can inhibit polypeptides including polypeptides released by action of the protease from forming or reforming cross-links with nucleic acids in the sample. The 2-imidazolidone by removing formaldehyde can also protect the protease from inactivation. Although 2-imidazolidone has previously been reported to be a formaldehyde scavenger, it is surprising that its potential inhibition of formation of new cross-links for a short period of incubation results in material improved availability of nucleic acids for capture, amplification and subsequent processing considering the long period of time for which samples may be stored and cross links can be formed before protease and 2-imidazolidone are supplied. It is also surprising that presence of 2-imidazolidone does not itself impair the ability of nucleic acids to undergo capture, amplification or other nucleic acid hybridization event because some imidazolines are known nucleic acid denaturants.

The methods can be used on any form of nucleic acid including DNA and RNA. DNA can be genomic or cDNA among others. RNA can be mRNA, rRNA, hnRNA, tRNA, or viral RNA among others. While DNA may be the desired analyte, RNA presents more stringent requirements for sample processing due to its chemical instability, including instability at high temperatures. Thus, procedures for isolating RNA were pursued for demonstrating the new method of sample preparation under the most rigorous conditions.

A model system for gynecologic specimen collection using a formaldehyde-containing liquid-based cytology preservative was employed to illustrate the nucleic acid isolation technique. In its practical application, this system involves first obtaining a swab of cervical cells, transferring the obtained sample of cells to SUREPATH (a registered trademark of TriPath Imaging, Inc.) liquid-based cytology preservative, and then processing the preserved cells for subsequent molecular testing. The molecular testing in this instance required in vitro amplification and detection of human papillomavirus (HPV) RNA target nucleic acids.

HPV is associated with the development of cervical cancer, and that detection of expressed HPV RNA has particular value as a diagnostic and monitoring assay. Indeed, HPV molecular testing in conjunction with cytology is now recommended for cervical cancer screening and patient management. Accordingly, it was reasoned that liquid Pap testing would be one example of an assay system that would benefit from enhancing recovery of amplifiable RNA by improved processing of samples preserved in formalin, or other liquid-based cytology preservatives containing formaldehyde. Moreover, automated testing procedures based on amplification nucleic acid in vitro followed by detection of HPV-specific amplification products would benefit as well.

The APTIMA® HPV genetic probe assay is a commercially available multiplex nucleic acid test that detects E6/E7 mRNA from 14 high-risk HPV genotypes (e.g., cat. no. 303585, Gen-Probe Incorporated, San Diego, Calif.). Among the genotypes detected are HPV 16, HPV 18, and HPV 45. This assay, which relies on target capture using a nucleic acid hybridization approach, has been demonstrated for use with cervical specimens preserved in THINPREP® liquid-based cytology preservative that does not include formaldehyde. The genetic probe assay also has been demonstrated for use with specimens preserved in SUREPATH® liquid-based cytology reagent after being first combined with a specimen transport medium (STM), and then treated with a reagent that includes relatively high levels of proteinase K enzyme (180 U/reaction). SUREPATH® liquid-based cytology preservative contains formaldehyde, ethanol, methanol, and isopropanol. Whereas specimens preserved in THINPREP can be processed rapidly for testing by the APTIMA® HPV genetic probe assay, specimens preserved in SUREPATH® require digestion with proteinase K for two hours at 65° C. This requirement compromises the utility of the latter preservative. By the improved method described below, specimens preserved in SUREPATH® liquid-based cytology reagent can be processed using less enzyme reagent and an incubation time of only 15 minutes.

Preferred Reagent Compositions

The disclosed technique for preparation of nucleic acid from formaldehyde-containing liquid-based cytology preservatives relies on the combined use of a protease enzyme and 2-imidazolidone. The disclosed technique further relies upon use of a protease enzyme at a high temperature. In a preferred approach, the protease enzyme begins in a lyophilized form that is reconstituted using a buffered solution that includes 2-imidazolidone. Preferably, the reconstitution buffer further includes EDTA. In one highly preferred embodiment, the protease enzyme is the proteinase K enzyme, which is known to retain activity within the broad range of pH 4.0-pH 12.0. However, the pH of the buffer used for reconstituting protease enzyme preferably falls in the range of from about pH 7.5 to about pH 8.5. This range permits optimal enzymatic activity while still protecting RNA from hydrolytic cleavage that occurs under strongly alkaline conditions. Still more preferably, the buffer used in the reconstitution buffer includes a Tris buffer at about pH 8.0.

The final concentrations of key reagent components, when combined with an optional diluent and the liquid-based cytology preservative that includes formaldehyde, fall within preferred ranges. The optional diluent can be a buffered solution that includes a detergent that lyses cell membranes. Exemplary detergents include anionic detergents such as sodium dodecyl sulfate (SDS), and lithium lauryl sulfate (LLS). Other detergents, such as the nonionic detergents, may also be useful. Advantageously, the strong ionic detergents can denature proteins, thereby rendering them better targets for proteolysis by the proteinase K enzyme. The final concentration (by molarity) of 2-imidazolidine in the reaction mixture preferably is selected to fall in a range that is 1-fold to 5-fold, or more preferably 2-fold to 5-fold the final maximum concentration of formaldehyde. Final concentration of 2-imdazolidone is determined the moles added over the volume of the reaction mixture after all reagents have been added. Final concentration of formaldehyde is the amount of moles present in the preservative used for making the specimen divided by the volume of the reaction mixture after all reagents have been added. In other words, no subtraction is made for formaldehyde consumed in inducing crosslinks before the heat incubation. For example, if a reaction mixture prepared by combining 1 ml of liquid-based cytology preservative (e.g., including a cellular specimen), 2.9 ml of a diluent, and 0.3 ml of a reagent including 2-imidazolidone, proteinase K enzyme, EDTA, and buffer had a final formaldehyde concentration of about 28 mM, then the final concentration of 2-imidazolidone at about 2-fold excess would be about 50 mM to about 60 mM. The final concentration of proteinase K enzyme advantageously can be reduced in the present formulation relative to the amount that would otherwise be used in the absence of 2-imidazolidone. Although practice of the invention is not dependent on an understanding of any particular mechanism of action, it is believed that proteinase K may serve to digest amine bonds connecting proteins to methyl bridges, thereby releasing nucleic acid and making it accessible for target capture in the hybridization-dependent target capture step of the APTIMA® assay. The final concentration of proteinase K enzyme preferably falls in the range of from about 43 U/ml to about 4.3 U/ml, with a concentration of about 10-11 U/ml being highly preferred. Thus, a reaction volume of 4.2 ml would preferably include about 40-50 U or 43 U of proteinase K enzyme. The final concentration of EDTA preferably falls in the range of from 10 mM to 100 mM, more preferably in the range of from 10 mM to 50 mM, and still more preferably in the range of from 30 mM to 40 mM. The final concentration of buffering agent is variable, based on the structure of the agent, but is sufficient to provide adequate buffer capacity to ensure RNA contained in the sample is not substantially degraded by alkaline hydrolysis. This requirement can be fulfilled by employing a final buffer concentration in the range of from at least 10 mM up to about 500 mM, more preferably up to about 250 mM, still more preferably up to about 100 mM, and yet still more preferably up to about 50 mM. A highly preferred final concentration range for buffer in the reaction mixture prior to incubation at elevated temperature is 10 mM to 50 mM.

The specimen can be combined with protease and 2-imidazolidone in any order. For example, the protease and 2-imidazolidone can be combined with the specimen simultaneously. Alternatively, the protease can be combined with the specimen first, followed by 2-imidazolidone, or vice a versa.

Both of the reconstitution buffer and lyophilized protease may be components of a kit, and may be combined shortly before use. That is to say, an end-user of the kit may reconstitute the lyophilized enzyme to prepare the enzyme reagent that includes, for example, 2-imidazolidone, proteinase K enzyme, EDTA, and pH buffer. Preferably, a single solution of the reagent kit includes 2-imidazolidone, EDTA, and pH buffer, but does not include the proteinase K enzyme. The proteinase K enzyme preferably is packaged in a separate vial of the kit, where the enzyme is in the form of a lyophilisate.

Preferred Target Enrichment Approaches

Before initiating the amplification reaction, it may be desirable to first enrich or isolate target nucleic acids using a target capture technique. In a preferred approach, nucleic acids from the reaction mixture incubated at elevated temperature following addition of a reagent including 2-imidazolidone and proteinase K enzyme are contacted with a solid support having disposed thereon an immobilized probe. According to one embodiment, target nucleic acids having been processed by treatment with the combination of 2-imidazolidone and protease enzyme under elevated temperature conditions in the presence of EDTA and a pH buffer hybridize directly to the immobilized capture probe in a sequence-specific fashion. In a different embodiment, a "target capture probe" serves to bridge the solid support-immobilized capture probe and the target nucleic acid that is to be amplified. General features of this approach are disclosed by Weisburg et al., in U.S. Pat. No. 6,534,273, the disclosure of this document being incorporated by reference herein. Regardless of which approach is chosen, it should be clear that hybridization involving the target nucleic acid that is to be amplified is an essential feature of the procedure.

A variant target capture approach that may be used in connection with the techniques disclosed herein, and that relies on nonspecific hybridization to the target that is to be amplified, is detailed in published U.S. patent application U.S. 2008/0286775 A1, the disclosure of this document being incorporated by reference herein. In accordance with the nonspecific hybridization approach, the capture probe includes at least one sequence that exhibits alternative base pairing properties for the target nucleic acid compared to standard base pairing (i.e., G:C and A:T/U bonding). The target nucleic acid purified by this nonspecific hybridization approach may be RNA or DNA, which is at least partially single-stranded. Again, it should be clear that this sequence-independent target capture approach still relies on nucleic acid hybridization.

The present data show that target capture can occur notwithstanding the presence of 2-imidazolidone and reports that some imidazolines cause denaturation of nucleic acids.

Preferred Nucleic Acid Amplification Methods

Examples of amplification methods useful in connection with the present invention include, but are not limited to:

transcription mediated amplification (TMA), single-primer nucleic acid amplification, nucleic acid sequence-based amplification (NASBA), the polymerase chain reaction (PCR), strand displacement amplification (SDA), self-sustained sequence replication (3SR), DNA ligase chain reaction (LCR) and amplification methods using self-replicating polynucleotide molecules and replication enzymes such as MDV-1 RNA and Q-beta enzyme. Methods for carrying out these various amplification techniques respectively can be found in U.S. Pat. No. 5,399,491, U.S. patent application Ser. No. 11/213,519, published European patent application EP 0 525 882, U.S. Pat. Nos. 4,965,188, 5,455,166, Guatelli et al., Proc. Natl. Acad. Sci. USA 87:1874-1878 (1990), International Publication No. WO 89/09835, U.S. Pat. No. 5,472,840 and Lizardi et al., Trends Biotechnol. 9:53-58 (1991). The disclosures of these documents which describe how to perform nucleic acid amplification reactions are hereby incorporated by reference.

Reaction Mechanism

Figure 6:
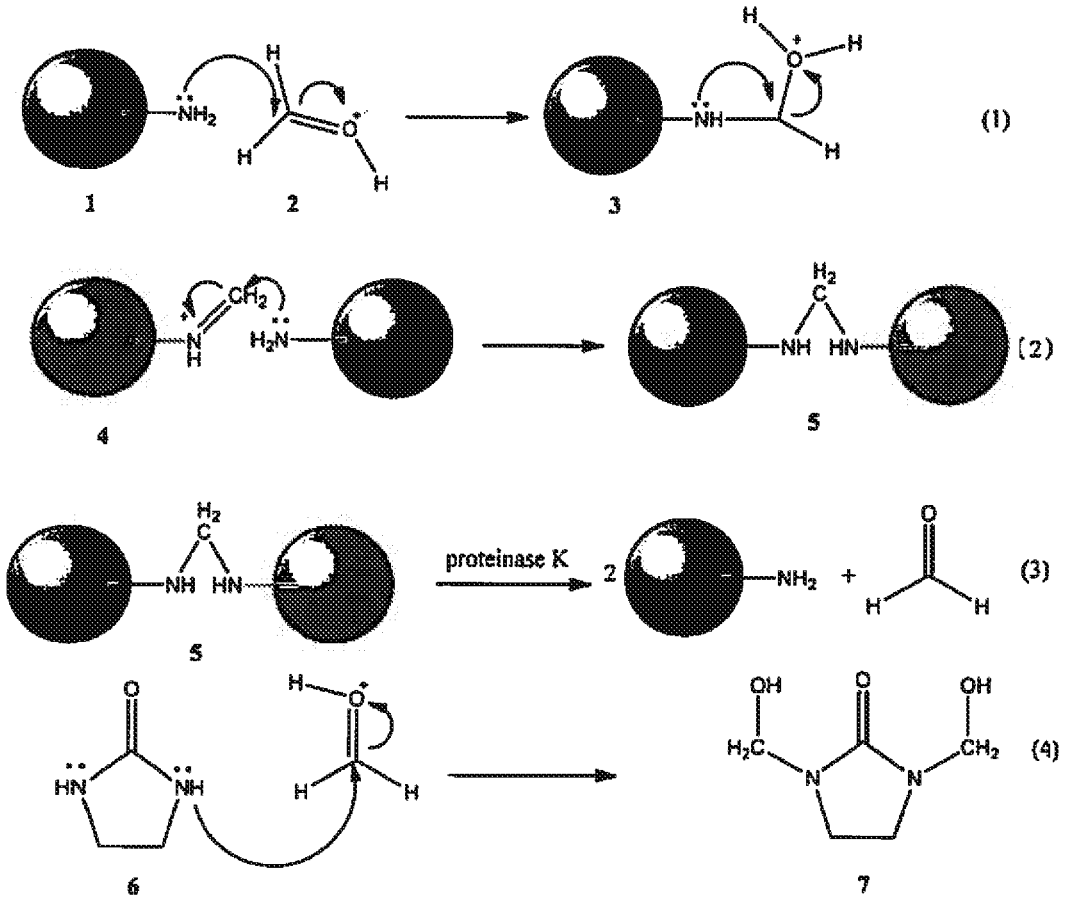
FIG. 6 shows a possible reaction mechanism of formaldehyde, proteinase K and 2-imidazolidone.

Although practice of the present methods is not depending on an understanding of mechanism, FIG. 6 illustrates a possible reaction mechanism underlying the methods. Under acidic conditions, formaldehyde 2 in a specimen can react with the nucleophilic functional groups of either nucleotides or polypeptides. Elimination of water then generates a reactive imine 4. A second nucleotide can then react with the imine to form the dimer 5. Proteinase K, which is a serine protease, hydrolyzes and cleaves the nitrogen-methylene linker. This cleavage can regenerate the starting nucleotides and formaldehyde. 2-imidazolidone, which is a formaldehyde scavenger, can react with two molecules of formaldehyde to generate an imidazolidone-methanol compound 7. This reaction effectively prevents the formaldehyde from reacting again with either the released nucleotides or polypeptides.

Sensitivity

Treatment of a specimen with a protease and 2-imidazolidone as just described can result in reversal of more modifications, particularly cross-links, on nucleic acids in the sample, more nucleic acids being freed from cross-linked polypeptides, greater yield of captured nucleic acid, greater yield of amplified nucleic acids, and improved assay sensitivity (i.e., lower threshold of a target DNA needed to be presence for a target). Such improvements can be measured relative to otherwise comparable controls in which the protease or the 2-imidazolidone or both is/are omitted. Preferably improvement is shown compared both with a control in which the protease is omitted and with a control in which the 2 imidazolidone is omitted. Improvement means an improvement of sufficient magnitude to make it beyond typical experimental variation ($p<0.05$). For example, in some methods, treatment can result in an improvement of at least 5%, 10%, 20%, or 30% of yield of nucleic acids freed from cross-links or captured nucleic acids or amplified nucleic acids. Presence of cross-links can be assessed by assays separating by molecular weight such as gel electrophoresis or various forms of column chromatography. In some methods, treatment results in at least 50, 60, 70, 80 or 90% of nucleic acid molecules being free of cross-links to polypeptides and thus potentially subject to a hybridization capture assay or amplification. In some methods, treatment results in a higher assay positivity (or lower threshold of detection) meaning that some samples yield a positive result (target nucleic acid present) after treatment in accordance with the present methods than in control treatments in which either protease or 2-imidazolidone is omitted.

Preferred Embodiments

The following Examples disclose experimental procedures carried out to demonstrate the benefits of treating specimens in a formaldehyde-containing liquid-based cytology preservative with the combination of 2-imidazolidone and proteinase K enzyme at an elevated temperature. In a preferred embodiment, this combination is used in the presence of Tris buffer and EDTA. In all instances, the SUREPATH liquid-based cytology preservative served as the model liquid-based preservative containing formaldehyde. In the descriptions that follow, "demodifier solution" refers to a pH-buffered solution (pH 8.0) that included EDTA (500 mM) and 2-imidazolidone (in the range of from 740 mM to 750 mM). Preferred buffers for use in the demodifier solution include Tris buffer. As used herein, "specimen transport medium" (STM) refers to a phosphate-buffered detergent solution which, in addition to lysing cells, protects released RNAs by inhibiting the activity of RNases that may be active in the sample undergoing testing. Preferred detergents that may be used in STM include sodium dodecyl sulfate (SDS) and lithium lauryl sulfate (LLS), with LLS being slightly more preferred. When samples of liquid-based cytology preservative containing formaldehyde are to be combined with the demodifier solution and proteinase K enzyme, lyophilized enzyme conveniently can be reconstituted with the demodifier solution, and an aliquot of the reconstituted enzyme solution can be added to a reaction vessel containing the liquid-based cytology preservative.

Example 1 describes procedures used to assess analytical sensitivity of the experimental system by testing panels that included in vitro transcripts for each of the 14 high risk HPV genotypes. Success of the nucleic acid processing technique involving treatment with 2-imidazolidone and proteinase K under elevated temperature conditions was measured by detection of HPV RNA using a commercially available assay. As indicated below, results showed that the treatment conditions did not compromise amplification and detection of HPV RNAs.

EXAMPLE 1

Establishing Analytical Sensitivity of the HPV Assay Using Synthetic Transcripts In vitro synthesized transcripts served as templates for amplification in conventional TMA reactions performed using the APTIMA® HPV genetic probe assay for amplification and detection of HPV RNA. The transcript copy number used for each different HPV type corresponded to the limit of detection (LOD) for the APTIMA HPV genetic probe assay that had been established in preliminary procedures using specimens preserved in THINPREP liquid-based cytology preservative (i.e., the model preservative that does not contain formaldehyde). The LOD is the copy level that leads to a minimum positivity of at least 95% for all specimens tested. In this instance, in vitro transcripts were all used at 20 to 600 copies/reaction, as appropriate.

Three different sample processing conditions were tested. First, in vitro transcripts were added to THINPREP® liquid-based cytology samples in STM (1 ml sample and 2.9 ml STM), and then processed according to directions from the manufacturer of the APTIMA® HPV genetic probe assay. Second, in vitro transcripts were added to clinical HPV-negative residual SUREPATH liquid-based cytology preservative specimens in STM (1 ml sample and 2.9 ml STM). Aliquots (3.9 ml each) of the mixture were combined with 100 μl of a proteinase K reagent (1.8 U/μl proteinase K in Tris buffer (pH 8.0), sodium azide, and $CaCl_2$), and then incubated for 2 hours at 65° C. Following the enzyme digestion step, the mixtures were processed according to directions from the manufacturer of the APTIMA HPV genetic probe assay. Finally, as in the second case, in vitro transcripts were added to clinical HPV-negative residual SUREPATH liquid-based cytology preservative specimens in STM. In this instance, 3.9 ml aliquots of each sample STM mix were combined with 0.3 ml of a proteinase K enzyme reagent that included 2-imidazolidone in Tris-EDTA buffer. This reagent had been prepared by reconstituting lyophilized proteinase K using the demodifier solution. The final mixtures included 36 mM EDTA, 36 mM Tris-HCl, about 53 mM 2-imidazolidone, and 43 U of proteinase K enzyme. Mixtures were incubated at 90° C. for 15 minutes, and then processed according to directions from the manufacturer of the APTIMA® HPV genetic probe assay. Following amplification and detection of HPV RNA, the frequency of positive HPV detection was compared among replicates.

FIG. 1 shows the results of the analytical sensitivity evaluation performed using in vitro transcripts. Assay positivity for the samples preserved in SUREPATH liquid-based cytology preservative was at least 95% for 11 of the 14 HPV genotypes; with 3 genotypes, HPV 56, 58 and 59 yielding 93.3, 91.7 and 90% positivity, respectively. These results were similar to those obtained for samples preserved in THINPREP liquid-based cytology preservative, and similar or better than samples that had been preserved in SUREPATH liquid-based cytology preservative and then treated with proteinase K enzyme alone. This established the utility of the HPV testing system, and showed that use of the combination of 2-imidazolidone and proteinase K enzyme under elevated temperature conditions did not substantially inhibit in vitro amplification and detection reactions.

Example 2 describes procedures used for assessing analytical sensitivity of the HPV assay by testing a panel of human cells containing HPV. Procedures were generally as described under Example 1, except that: (1) HPV-expressing cell lines were used in place of in vitro transcripts; and (2) the samples were incubated in the presence of the formaldehyde-containing preservative for an extended period.

EXAMPLE 2

Establishing Analytical Sensitivity of the HPV Assay Using Human Cell Lines Containing HPV Human cell lines containing HPV were spiked into specimen pools of the SUREPATH liquid-based cytology preservative, stored for 7 days at 25° C., and then tested at half-log dilutions (3 to 30 cells/reaction) after treatment with either the combination of the demodifier solution and proteinase K at 90° C. for 15 minutes, or proteinase K alone at 65° C. for 2 hours. As in Example 1, the combination of demodifier solution and proteinase K was conveniently delivered as a single aliquot by reconstituting lyophilized proteinase K with the demodifier solution. Of course, there is no requirement for combining the reagents in this fashion. Cells used in this procedure were: (1) SiHa cells (expressing HPV16); (2) HeLa cells (expressing HPV 18); and (3) MS751 cells (expressing HPV 45). Again, HPV nucleic acids were captured, amplified and detected using the APTIMA HPV genetic probe assay in accordance with the manufacturer's instructions. The positivity of samples treated under the two conditions was compared.

Figure 2A:
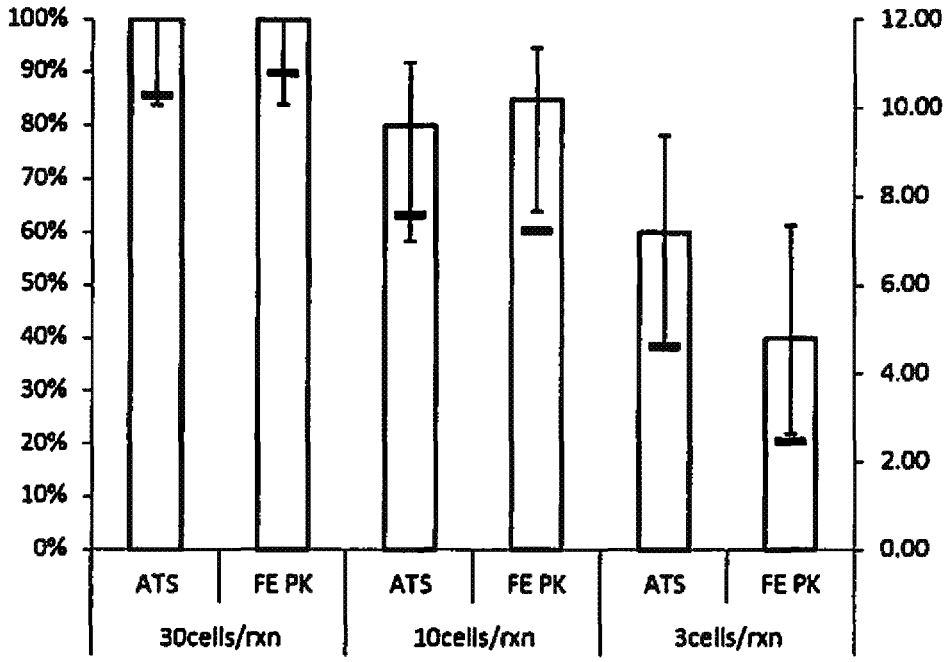
FIGS. 2A-2C are bar graphs showing % positivity in the HPV RNA amplification and detection assay performed using human cell lines containing different HPV types.
Figure 2B:
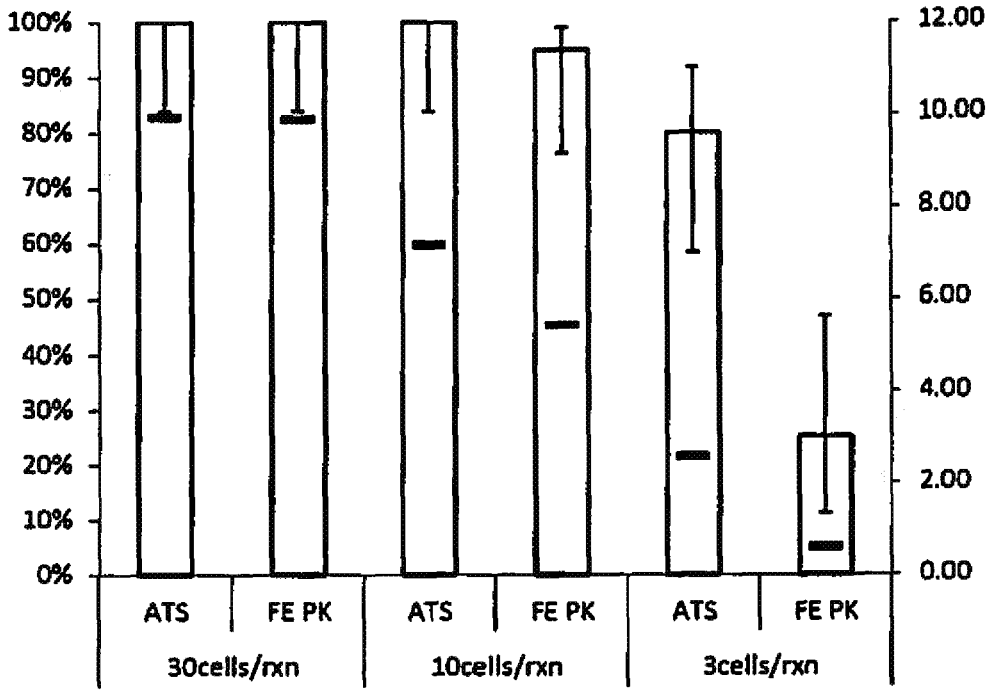
Figure 2C:
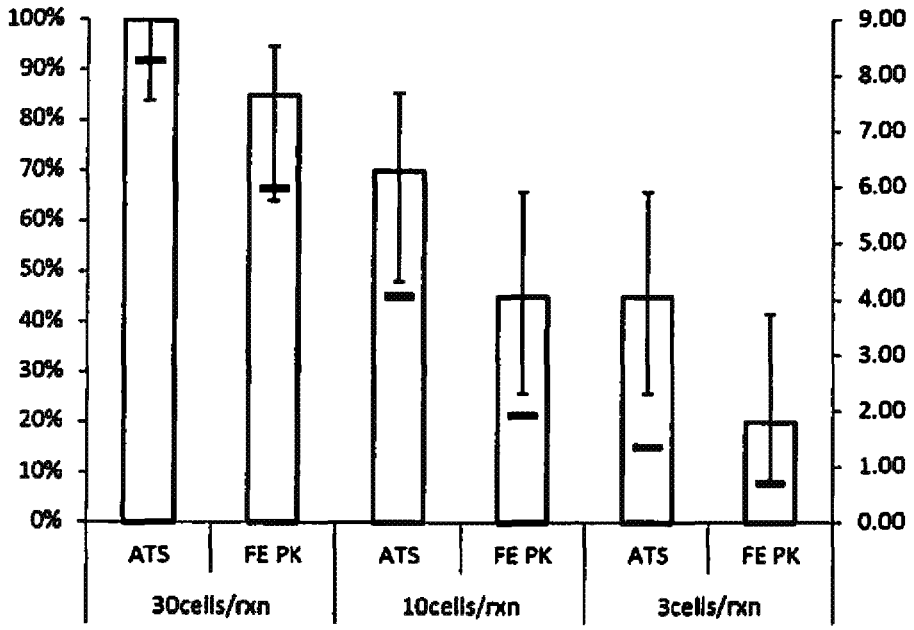

FIGS. 2A-2C show the analytical sensitivity results obtained using cell lines that had been stored for 7 days at 25° C. in SUREPATH liquid-based cytology preservative. Assay positivity for all three HPV-positive cell lines in samples treated with the combination of the demodifier solution and proteinase K enzyme was at least 95% at concentrations of 30, 10 and 30 cells/reaction for SiHa, HeLa and MS751 cells, respectively. These results were similar or better than results obtained using samples that had been stored 7 days at 25° C. in SUREPATH liquid-based cytology preservative and then treated with proteinase K enzyme alone. The most dramatic differences were observed in the trials using HeLa cells at the lowest input cell count. There was a clear statistically significant advantage to the sample processing treatment using 2-imidazolidone in combination with proteinase K and high temperature.

Example 3 describes procedures that demonstrated how the combined use of 2-imidazolidone and proteinase K under elevated temperature conditions led to improved recovery of amplifiable nucleic acid from samples stored for extended periods in a liquid-based cytology preservative containing formaldehyde. As discussed below, the difference in RNA recovery relative to trials treated with proteinase K alone was most noticeable at extended time periods.

EXAMPLE 3

Enhancing Recovery of Amplifiable mRNA from Cellular Specimens Stored in a Liquid-Based Cytology Preservative Containing Formaldehyde To mimic clinical specimens, ten pools of residual specimens in SUREPATH liquid-based cytology preservative, previously determined to be HPV-negative using the APTIMA HPV genetic probe assay, were split in half and spiked with either SiHa or HeLa cells. All tubes were stored neat at 25° C. for up to 42 days. Aliquots from each pool were diluted in a 1:2.9 SUREPATH:STM matrix to final cell concentrations of 30 and 100 cells/reaction on each day of testing. Samples were processed either by treatment with proteinase K alone for 2 hours at 65° C., or with the combination of demodifier solution and proteinase K (the combination being delivered as a single aliquot of proteinase K reconstituted with demodifier solution) for 15 minutes at 90° C. Again, HPV nucleic acids were captured, amplified and detected using the APTIMA HPV genetic probe assay in accordance with the manufacturer's instructions.

Figure 3A:
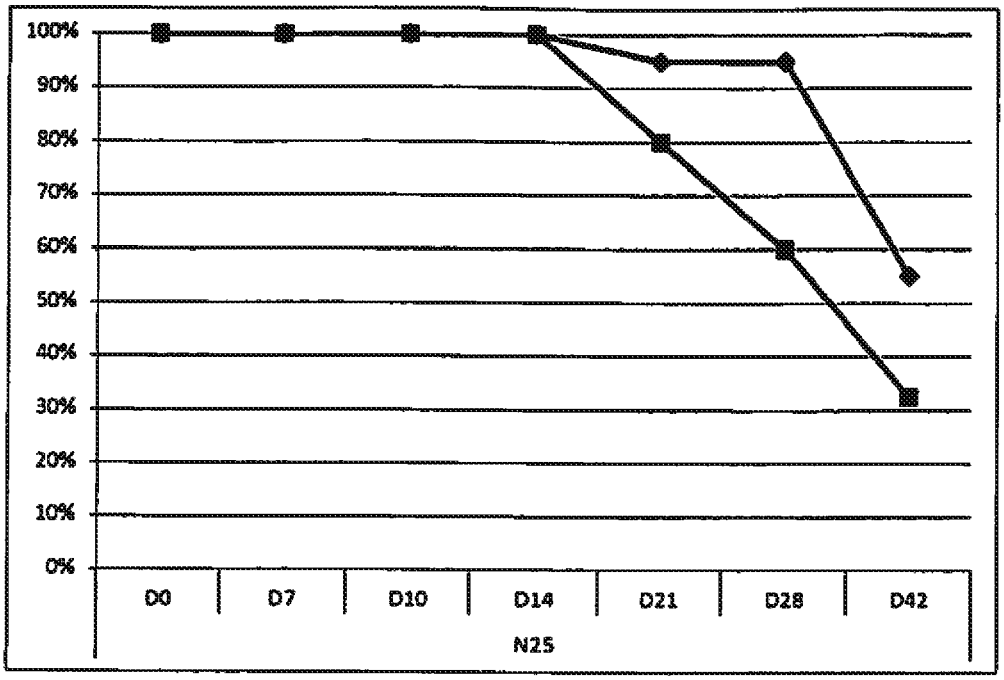
FIGS. 3A-3B are line graphs showing % positive reactions (vertical axis) as a function of time (days stored in liquid-based cytology preservative containing formaldehyde). Both graphs present results from procedures carried out using 30 cells/reaction.
Figure 3B:
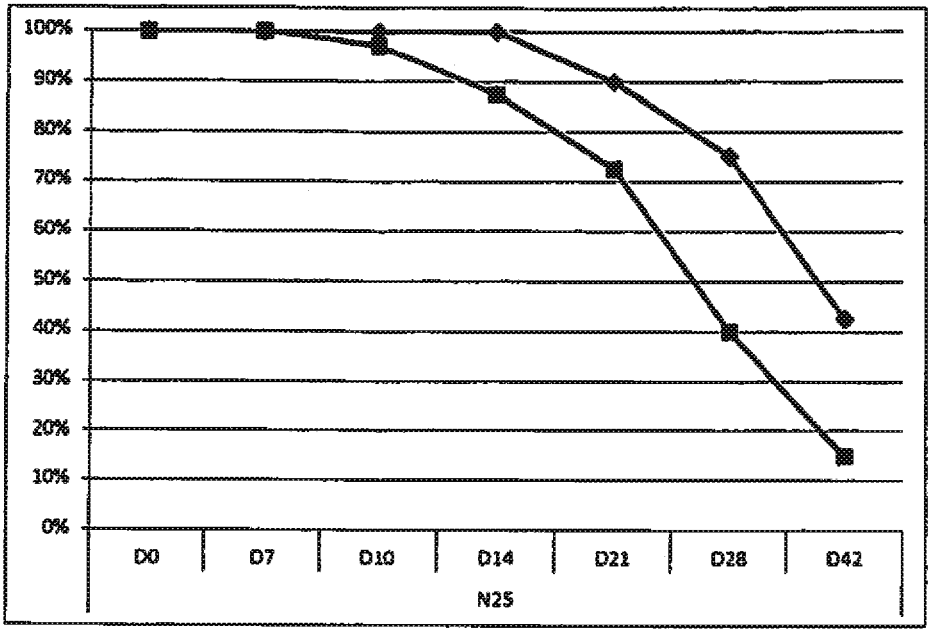

FIGS. 3A-3B present results supporting the advantages of sample processing that included treatment with the combination of 2-imidazolidone and proteinase K under elevated temperature conditions, relative to treatment with proteinase K alone. All results during this study were valid. At 30 cells per reaction, both SiHa and HeLa cells treated with the combination of 2-imidazolidone and proteinase K (e.g., proteinase K reconstituted with demodifier solution) maintained 100% positivity out to Day 14. Beyond this storage period, the combination treatment enhanced recovery of amplifiable RNA to a greater extent than treatment with proteinase K alone. At 100 cells/reaction, HeLa cells maintained 100% positivity out to Day 28, while SiHa cells remain 100% positive until Day 21 (data not shown).

Example 4 describes the procedure used to demonstrate that clinical samples stored in a formaldehyde-containing liquid-based cytology preservative could be treated with the combination of 2-imidazolidone and proteinase K under elevated temperature conditions and then processed to yield substantially constant amounts of RNA, regardless of the length of time the clinical sample had been stored.

EXAMPLE 4

Combination Treatment Permits Efficient Recovery of RNA for Clinical Samples Over Extended Storage Periods Thirty verified HPV-positive clinical specimens in SUREPATH liquid-based cytology preservative, obtained from a referral population, were evaluated in this study. An aliquot (0.5 ml) of each specimen was added to 2.9 ml STM and then diluted 1:10 and 1:100 in a 0.5:2.9 SP:STM matrix. Dilutions were stored at 4° C. and then tested at various time points for 120 days with the APTIMA HPV genetic probe assay (N=4 for each sample, 120 total replicates per time point). On each day of testing, 1 ml aliquots of the samples were mixed with 2.9 ml of STM and 0.3 ml of a reagent that included proteinase K reconstituted in demodifier solution to a final concentration of 143 U/ml of proteinase K. Mixtures were incubated at 90° C. for 15 minutes, processed to isolate nucleic acids by a target capture protocol, and tested with the APTIMA HPV genetic probe assay on an automated testing instrument.

Figure 4:
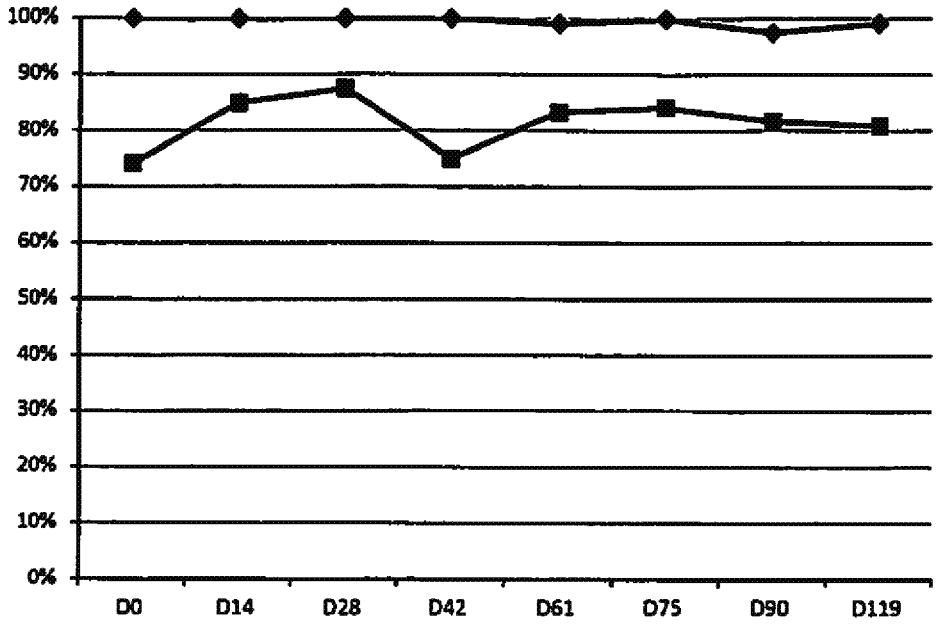
FIG. 4 is a line graph showing % positivity as a function of storage time at 2-8° C. The lines represent results for a clinical specimen diluted 1:10 (♦), and diluted 1:100 (▩).

FIG. 4 presents results showing that clinical specimens preserved in a liquid-based cytology preservative containing formaldehyde could be treated with the combination of 2-imidazolidone and proteinase K under elevated temperature conditions for a short time period to result in substantially constant recovery of RNA. All specimens that had been diluted 1:10 maintained at least 97.5% positivity after 120 days of storage at 4° C. Positivity for all 30 specimens diluted 1:100 ranged from 74.2% to 87.5% over the course of the study, with no consistent decrease in positivity observed.

EXAMPLE 5

Temperature Dependence

Target preparation: Tubes containing HPV18-infected HeLa cells were thawed at 37° C. and pooled into one tube. Phosphate-buffered saline was added to the tube and the tube was spun in a centrifuge at 1100 rcf to form a cell pellet. The supernatant was removed by pipetting. A pool of HPV-negative SurePath® clinical specimen derived from cell pellets (NCPP) was added to simulate a SurePath clinical specimen. The tube containing HeLa cells and NCPP was inverted to break up the pellet and incubated at 25° C. (concentration: 1000 cells/mL). After 0, 7, and 14 days, an aliquot from the tube was removed, STM was added, and dilutions were performed to a final concentration of 10 cells/reaction (final ratio of NCPP:STM 1:2.9). Tubes were treated (see next section) and tested using an APTIMA® HPV kit according to manufacturer's instructions.

Treatment methods: After 25° C. incubation and STM addition (see previous section) tubes were divided into 3 groups. Heat: 300 μL TE (concentration in tube: 36 mM Tris, 36 mM EDTA) was added to reaction tubes. Tubes were capped, placed in a 90° C. water bath for 15 minutes, and tested on APTIMA HPV. PK: 50 mg proteinase K was dissolved in 1 mL Fast Express diluent. 100 μL of the PK solution was added to reaction tubes (180 units proteinase K per tube). Tubes were capped, placed in a 65° C. water bath for 2 hours, and tested on APTIMA HPV. Heat+PK: 50 mg proteinase K was dissolved in 12 mL TE. 300 μL of the TE+PK solution was added to reaction tubes (concentration in tube: 36 mM Tris, 36 mM EDTA, 45 units PK). Tubes were capped, placed in a 90° C. water bath for 15 minutes, and tested an APTIMA® HPV kit according to manufacturer's instructions. Results are presented in Table 1.

TABLE 1

| Time Point | Heat | PK | Heat + PK |
|---|---|---|---|
| D0 | 100% | 100% | 100% |
| D7 | 60% | 85% | 90% |
| D14 | 25% | 50% | 75% |

N = 20

These data indicates that the combined treatment was most effective on samples having undergone the longest storage. Moreover, samples treated with proteinase K at a high temperature resulted in a greater recovery that did those treated with proteinase K at low temperature or treated with a high temperature alone.

EXAMPLE 6

Formaldehyde Scavengers, Proteinase K and High Temperature

Targets were prepared substantially as described above in Example 5. Briefly, HeLa cell lines (HPV-18+), SiHa cell lines (HPV-16+), MS751 cell lines (HPV-45+) and Trichomonas cell lines (Trichomonas+) were incubated for 7 days in SurePath solution. After 7 days an aliquot of each SurePath cell sample was then combined into a condition as illustrated in Table 2.

TABLE 2

| Condition | Formulation* |
|---|---|
| 1 | Proteinase K |
| 2 | Proteinase K and Tris/EDTA |
| 3 | Proteinase K, Tris/EDTA and 1X 2-Imidazolidone** |
| 4 | Proteinase K, Tris/EDTA and 2X 2-Imidazoladone** |
| 5 | Proteinase K, Tris/EDTA and succinic acid dihydrazide |

*HeLa and SiHa cells were incubated in the presence of 180 U proteinase K and in the presence of 45 U proteinase K.
**1X and 2X refer to the molar concentration of 2-imidazolidone in the solution. 1X means that the molar concentration was about equivalent to that of the formaldehyde in the solution; 2X means it was twice that of formaldehyde.

The combined solutions were then incubated for either 15 minutes or for 2 hours and at a temperature of either 65° C. or 90° C. Incubation conditions are illustrated in Table 3.

TABLE 3

| Treatment | Cell Line | Condition | Temperature | Time |
|---|---|---|---|---|
| 1 | HeLa | 1 | 65° C. | 2 hours |
| 2 | HeLa | 2 | 90° C. | 15 minutes |
| 3 | HeLa | 3 | 90° C. | 15 minutes |
| 4 | HeLa | 4 | 90° C. | 15 minutes |
| 5 | HeLa | 5 | 90° C. | 15 minutes |
| 6 | SiHa | 1 | 65° C. | 2 hours |
| 7 | SiHa | 2 | 90° C. | 15 minutes |
| 8 | SiHa | 3 | 90° C. | 15 minutes |
| 9 | SiHa | 4 | 90° C. | 15 minutes |
| 10 | SiHa | 5 | 90° C. | 15 minutes |
| 11 | MS715 | 1 | 65° C. | 2 hours |
| 17 | MS715 | 2 | 90° C. | 15 minutes |
| 13 | MS715 | 5 | 90° C. | 15 minutes |
| 14 | Trichomonas | 1 | 65° C. | 2 hours |
| 15 | Trichomonas | 2 | 90° C. | 15 minutes |
| 16 | Trichomonas | 4 | 90° C. | 15 minutes |

Following incubations, the samples were assayed to determine nucleic acid recovery under the various treatments. In a first assay, 3 cells/reaction of HeLa cells from conditions 1-4 and 10 cells/reaction of SiHa cells from conditions 1-4 (see Table 3) were assayed using an APTIMA HPV kit (catalog no. 303585, Gen-Probe Incorporated) generally according to manufacturer's instructions. In a second assay, 0.05 cells/reaction of Trichomonas cells from conditions 1, 2 & 4 (see Table 3) were assayed using an APTIMA Trichomonas vaginalis assay (catalog no. 303563, Gen-Probe Incorporated) generally according to manufacturer's instructions. In a third assay, 3 cells/reaction of each of HeLa, SiHa and MS751 cells from conditions 1, 2 & 5 (See Table 3), each incubated with 45 U of proteinase K, were assayed using an APTIMA HPV kit (catalog no. 303585, Gen-Probe Incorporated) generally according to manufacturer's instructions. In a fourth assay, 3 cells/reaction of each of HeLa, SiHa and MS751 cells from conditions 1, 2 & 5 (See Table 3), each incubated with 45 U of proteinase K, were assayed using an APTIMA HPV genotyping kit (catalog no. 303234, Gen-Probe Incorporated) generally according to manufacturer's instructions. Results are presented in Tables 4 to 7.

TABLE 4

HPV Detection Assay and 180 U Proteinase K

| First Assay | Treatment | Cell Line | Condition | Temp | Time | % Positive |
|---|---|---|---|---|---|---|
| | 1 | HeLa | 1 | 65° C. | 2 hours | 33% |
| | 2 | HeLa | 2 | 90° C. | 15 minutes | 73% |
| | 3 | HeLa | 3 | 90° C. | 15 minutes | 78% |
| | 4 | HeLa | 4 | 90° C. | 15 minutes | 83% |
| | 6 | SiHa | 1 | 65° C. | 2 hours | 80% |
| | 7 | SiHa | 2 | 90° C. | 15 minutes | 83% |
| | 8 | SiHa | 3 | 90° C. | 15 minutes | 92% |
| | 9 | SiHa | 4 | 90° C. | 15 minutes | 90% |

TABLE 5

Trichomonas vaginalis Assay and 180 U Proteinase K

| Second Assay | Treatment | Cell Line | Condition | Temp | Time | % Positive |
|---|---|---|---|---|---|---|
| | 14 | Trichomonas | 1 | 65° C. | 2 hours | 33% |
| | 15 | Trichomonas | 2 | 90° C. | 15 minutes | 67% |
| | 16 | Trichomonas | 4 | 90° C. | 15 minutes | 97% |

TABLE 6

HPV Detection Assay and 45 U of Proteinase K

| Third Assay | Treatment | Cell Line | Condition | Temp | Time | % Positive |
|---|---|---|---|---|---|---|
| | 1 | HeLa | 1 | 65° C. | 2 hours | 30% |
| | 2 | HeLa | 2 | 90° C. | 15 minutes | 40% |
| | 5 | HeLa | 5 | 90° C. | 15 minutes | 85% |
| | 6 | SiHa | 1 | 65° C. | 2 hours | 75% |
| | 7 | SiHa | 2 | 90° C. | 15 minutes | 70% |
| | 10 | SiHa | 5 | 90° C. | 15 minutes | 90% |
| | 11 | MS715 | 1 | 65° C. | 2 hours | 15% |
| | 12 | MS715 | 2 | 90° C. | 15 minutes | 30% |
| | 13 | MS715 | 5 | 90° C. | 15 minutes | 30% |

TABLE 7

HPV Genotyping Assay and 46 U of Proteinase K

| Fourth Assay | Treatment | Cell Line | Condition | Temp | Time | % Positive |
|---|---|---|---|---|---|---|
| | 1 | HeLa | 1 | 65° C. | 2 hours | 30% |
| | 2 | HeLa | 2 | 90° C. | 15 minutes | 40% |
| | 5 | HeLa | 5 | 90° C. | 15 minutes | 85% |
| | 6 | SiHa | 1 | 65° C. | 2 hours | 75% |
| | 7 | SiHa | 2 | 90° C. | 15 minutes | 70% |
| | 10 | SiHa | 5 | 90° C. | 15 minutes | 90% |
| | 11 | MS715 | 1 | 65° C. | 2 hours | 15% |
| | 12 | MS715 | 2 | 90° C. | 15 minutes | 30% |
| | 13 | MS715 | 5 | 90° C. | 15 minutes | 30% |

These data show that specimens preserved in a liquid-based cytology preservative containing formaldehyde could be treated with the combination of a formaldehyde scavenger, proteinase K and an elevated temperature for a short time period to result in substantially constant recovery of RNA. These data further show formulations containing proteinase K that are useful at high temperatures known to denature and inactivate proteinase K and further known to destroy RNA, and yet provide superior nucleic acid recovery compared to recovery at lower temperatures. These data further show that formulations that allow for recovery of nucleic acids from a formalin containing solution using a reduced concentration of protease.

EXAMPLE 7

The following assay was performed to determine the percent recovery of RNA from samples that had been treated for 7 days with a SurePath® reagent, the samples being treated with proteinase K for 15 minutes at a number of high temperatures. Samples were prepared substantially as described in Example 6. Briefly, HeLa cell lines (HPV-18+) and SiHa cell lines (HPV-16 +) were incubated for 7 days and at 25° C. in Surepath®. After 7 days and aliquot of each SurePath® cell sample was then combined into condition 3 as illustrated in Table 2, above. The combined solutions were then incubated at a number of temperatures for 15 minutes and assayed using an HPV detection kit (catalog no. 303585, Gen-Probe Incorporated), as presented in Table 8.

TABLE 8

| Temperature | % Positive HeLa @ 3 cells/reaction | % Positive SiHa @ 10 cells/reaction |
|---|---|---|
| 85° C. | 88% | 95% |
| 90° C. | 85% | 93% |
| 95° C. | 98% | 95% |

The following assay was performed to determine the percent recovery of RNA from samples that had been treated for 7 days with a SurePath® reagent, the samples being treated with proteinase K at 90° C. for a number of short incubation times. Samples were prepared substantially as described in Example 6. Briefly, HeLa cell lines (HPV-18+) and SiHa cell lines (HPV-16+) were incubated for 7 days and at 25° C. in Surepath®. After 7 days and aliquot of each SurePath® cell sample was then combined into condition 3 as illustrated in Table 2, above. The combined solutions were then incubated at 90° C. for a number of minutes, and then assayed using an HPV detection kit (catalog no. 303585, Gen-Probe Incorporated), as presented in Table 9.

TABLE 9

| Time | Positive HeLa @ 3 cells/reaction | % Positive SiHa @ 10 cells/reaction |
|---|---|---|
| 13 minutes | 80% | 93% |
| 15 minutes | 85% | 93% |
| 17 minutes | 93% | 90% |
| 20 minutes | 95% | 95% |

The following assay was performed to determine the percent recovery of RNA from samples that had been treated for 7 days with a SurePath® reagent, the samples being treated with a number of concentrations of proteinase K at 90° C. for a 15 minute incubation time. Samples were prepared substantially as described in Example 6. Briefly, HeLa cell lines (HPV-18+) and SiHa cell lines (HPV-16+) were incubated for 7 days and at 2° C. in Surepath®. After 7 days and aliquot of each SurePath cell sample was then combined into condition substantially like condition 3 illustrated in Table 2, above, with the exception that the proteinase K concentrations listed in Table C. The combined solutions were then incubated at 90° C. for 15 minutes, and then assayed using an HPV detection kit (catalog no. 303585, Gen-Probe Incorporated), as presented in Table 10.

TABLE 10

| U of proteinase K | % Positive HeLa @ 3 cells/reaction | % Positive SiHa @ 10 cells/reaction |
|---|---|---|
| 39.6 U | 83% | 90% |
| 43.0 U | 83% | 93% |
| 46.4 U | 85% | 90% |

The following assay was performed to determine the percent recovery of RNA from samples that had been treated for 7 days with a SurePath reagent, the samples being treated with a number of concentrations of 2-imidazolidone at 90° C. for a 15 minute incubation time. Samples were prepared substantially as described in Example 6. Briefly, HeLa cell lines (HPV-18+) and SiHa cell lines (HPV-16+) were incubated for 7 days and at 25° C. in Surepath. After 7 days and aliquot of each SurePath cell sample was then combined into condition substantially like condition 3 illustrated in Table 2, above, with the exception that the 2-imidazolidone concentrations listed in Table D. The combined solutions were then incubated at 90° C. for 15 minutes, and then assayed using an HPV detection kit (catalog no. 303585, Gen-Probe Incorporated), as presented in Table 11.

TABLE 11

| mM 2-imidazolidone | % Positive HeLa @ 3 cells/reaction | % Positive SiHa @ 10 cells/reaction |
|---|---|---|
| 26.6 mM | 78% | 95% |
| 47.9 mM | 80% | 93% |
| 53.2 mM | 83% | 93% |
| 58.6 mM | 75% | 90% |
| 106.5 mM | 75% | 90% |

For all assays, the number of replicates was 40

EXAMPLE 8

Figure 5:
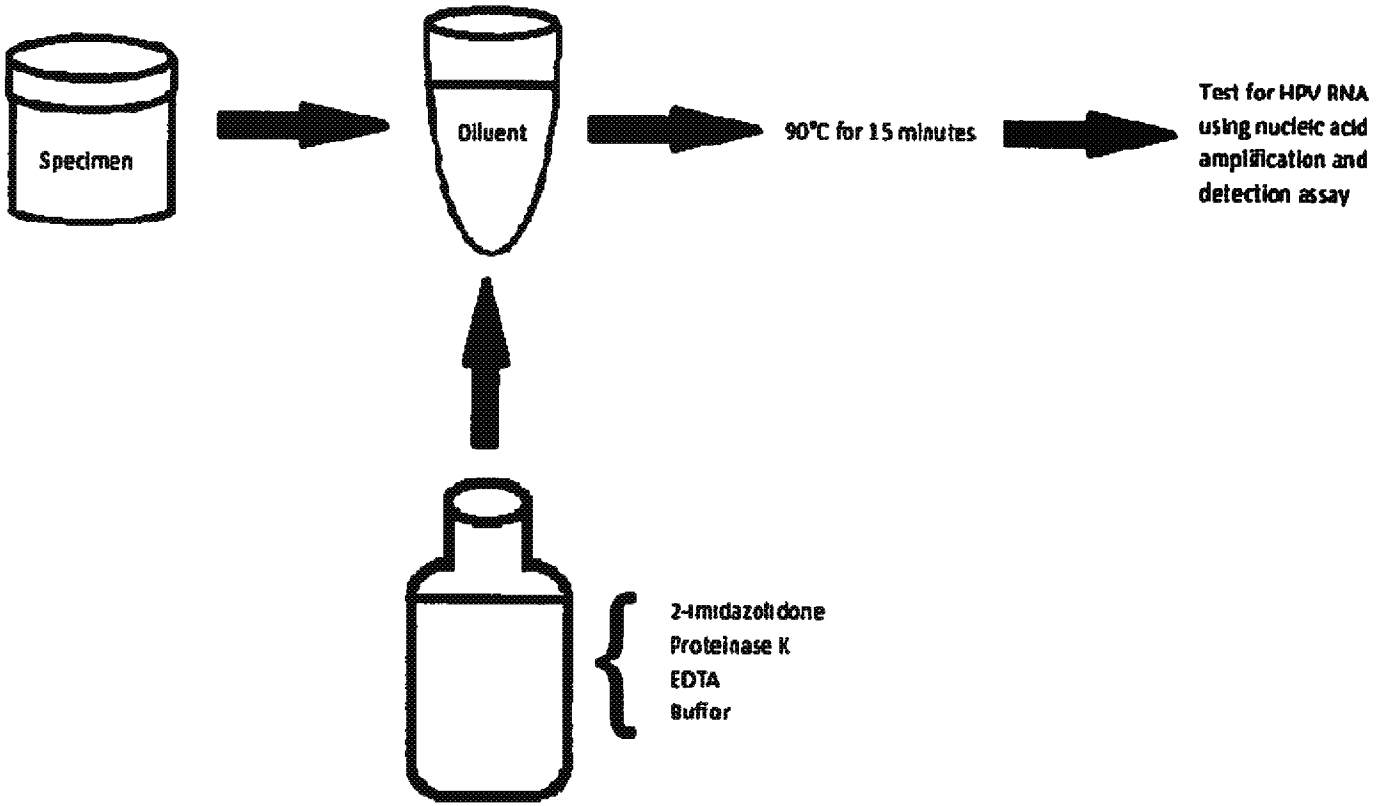
FIG. 5 is a diagram depicting key elements of an exemplary workflow.

Work Flow Incorporating Processing of Specimens Preserved in a Liquid-Based Cytology Preservative that Includes Formaldehyde Example 8 describes a typical work flow for processing clinical samples. A clinical sample obtained using a swab device is introduced into a vial containing a liquid-based cytology preservative that includes formaldehyde, and the vial is capped securely. SUREPATH liquid-based cytology preservative can be used as the liquid-based cytology preservative. Cellular material dispersed in the liquid contents of the vial is transported to a clinical laboratory for testing, including molecular analysis of nucleic acid. At the clinical laboratory an aliquot of the vial is mixed with an aliquot of a diluent, such as a buffered detergent solution. A phosphate-buffered detergent solution is one example of a preferred diluent. The detergent used in this application preferably is an anionic detergent, such as sodium dodecyl sulfate (SDS) or lithium lauryl sulfate (LLS). The mixture is further combined with 2-imidazolidone and a protease. The protease used for this purpose may be the proteinase K enzyme. In a simplified approach, lyophilized proteinase K is reconstituted in a solution that includes a pH buffer, EDTA, and 2-imidazolidone. The pH buffer may be a Tris buffer, and the reconstituted enzyme solution may have a pH of about 8.0. The final mixture that includes the diluted clinical sample, the 2-imidazolidone and the protease enzyme is then heated to an elevated temperature for between 5 minutes and 30 minutes. The mixture is preferably heated to about 90° C. for about 15 minutes. Nucleic acid in the sample is rendered suitable for purification and use as a template in an in vitro amplification reaction. For example, RNA is purified by capture onto a solid support, for example using sequence-specific hybridization to an immobilized nucleic acid strand, and then amplified in a nucleic acid amplification reaction. The nucleic acid amplification reaction may be a Transcription Mediated Amplification (TMA) reaction. Amplification products are contacted with a sequence-specific hybridization probe to determine the presence or absence of a particular target sequence. The particular target sequence may be an HPV target sequence. The workflow is depicted in FIG. 5.

This invention has been described with reference to a number of specific examples and embodiments thereof. Of course, a number of different embodiments of the present invention will suggest themselves to those having ordinary skill in the art upon review of the foregoing detailed description. Thus, the true scope of the present invention is to be determined upon reference to the appended claims. Unless otherwise apparent from the context, any embodiment, aspect, step or feature of the invention can be used with any other.

What is claimed is:

1. A method of isolating a nucleic acid from processing a specimen that includes a clinical sample disposed in a liquid-based cytology preservative that comprises formaldehyde, the method comprising the steps of:

(a) combining the specimen with a protease enzyme and a formaldehyde scavenger that is 2-imidazolidone to create a reaction mixture;

(b) incubating the reaction mixture at an elevated temperature for a period of time sufficient to reverse chemical modifications of nucleic acid that may be contained in the specimen by formaldehyde in the liquid-based cytology preservative; and (c) isolating a nucleic acid from the reaction mixture after the incubating step.

2. The method of claim 1, wherein the reversing releases nucleic acids in the specimen from formaldehyde-induced crosslinking to polypeptides in the specimen.

3. The method of claim 2, wherein the protease enzyme frees the nucleic acids from the formaldehyde-induced crosslinking.

4. The method of claim 1, wherein the clinical sample has been disposed in the liquid-based cytology preservative for from about 7 to about 120 days before performing step (a).

5. The method of claim 1, wherein the incubating step is for a period of time no greater than 30 minutes.

6. The method of claim 1, wherein at least 90% of the chemical modifications of the nucleic acid molecules in the specimen are reversed after the incubating step.

7. The method of claim 1, wherein final concentration of the 2-imidazolidone before the incubation step is from about 1 to about 5 fold by moles greater than the final maximum concentration of the formaldehyde.

8. The method of claim 7, wherein the protease enzyme is proteinase-K present at a concentration of from about 4.3 to about 43 U/ml.

9. The method of claim 1, wherein the temperature of the incubating step is about 90° C.

10. The method of claim 1, wherein the protease enzyme and formaldehyde scavenger are combined simultaneously with the specimen.

11. The method of claim 1, wherein the protease enzyme is combined with the specimen before formaldehyde scavenger.

12. The method of claim 1, wherein the formaldehyde scavenger is combined with the specimen before the protease enzyme.

13. The method of claim 1, wherein the clinical sample comprises RNA.

14. The method of claim 13, wherein the isolated nucleic acid is RNA.

15. The method of claim 1, wherein the nucleic acid is isolated in step (c) by a target capture assay with a target capture probe hybridizing to the nucleic acid to be isolated and to an immobilized probe that is immobilized to a solid support.

16. The method of claim 13, wherein the isolated nucleic acid is human papillomavirus (HPV) RNA target nucleic acid.

17. The method of claim 1, wherein the specimen is a cervical cell clinical sample disposed in a liquid-based cytology preservative.

18. The method of claim 1, wherein the protease enzyme is proteinase-K present at a concentration of from about 4.3 to about 43 U/ml.

19. The method of claim 15, wherein the solid support comprises a magnetic bead.

20. The method of claim 1, wherein the incubating step is for a period of time between about 5 minutes and about 30 minutes.

21. The method of claim 1, wherein the incubating step is for a period of time between about 5 minutes and about 15 minutes.

22. The method of claim 1, wherein the incubating step is for a period of time no greater than 15 minutes.

23. The method of claim 1, wherein the temperature of the incubating step is from about 91° C. to about 95° C.

24. The method of claim 5, wherein the temperature of the incubating step is from about 60° C. to about 100° C.

25. The method of claim 1, wherein the temperature of the incubating step is from about 85° C. to about 95° C.

*26. The method of claim 1, wherein the incubating temperature is in the range of 80° C. to 100° C.*

*27. The method of claim 26, wherein the nucleic acid isolated is RNA.*

*28. The method of claim 1, wherein the incubating temperature is at least 80° C.*

*29. The method of claim 28, wherein the nucleic acid isolated is RNA.*

*30. The method of claim 1, wherein the protease enzyme is proteinase-K.*

*31. The method of claim 30, wherein the incubating temperature is in the range of 80° C. to 100° C.*

*32. The method of claim 31, wherein the nucleic acid isolated is RNA.*

*33. The method of claim 1, wherein step (a) is performed using a nucleic acid processing system comprising (i) a programmable controller, (ii) a pipetting device in communication with the programmable controller, (iii) a first holder for a reaction vial, and (iv) a second holder for a reagent vial, and wherein the programmable controller is configured by software instructions to cause the pipetting device to transfer an aliquot of liquid from the reagent vial to the reaction vial.*

*34. The method of claim 33, wherein the reaction vial contains the specimen before the pipetting device transfers an aliquot of liquid from the reagent vial to the reaction vial.*

*35. A method of isolating RNA from a specimen that includes a clinical sample disposed in a liquid-based cytology preservative that comprises formaldehyde, the method comprising the steps of:*

*(a) combining the specimen with a protease enzyme and a hydrazine- or hydrazide-containing formaldehyde scavenger;*

*(b) incubating the reaction mixture at a temperature in the range of 80° C. to 100° C. for a period of time sufficient to reverse chemical modifications of RNA that may be contained in the specimen by formaldehyde in the liquid-based cytology preservative; and*

*(c) isolating RNA from the reaction mixture after the incubating step.*

*36. The method of claim 35, wherein the protease enzyme is proteinase-K.*

*37. The method of claim 35, wherein the formaldehyde scavenger is succinic acid dihydrazide.*

*38. A system for processing nucleic acid containing samples preserved in a liquid-based cytology preservative that comprises formaldehyde, the system comprising:*

*a programmable controller;*

*a pipetting device in communication with the programmable controller;*

*a first holder for a reaction vial;*

*a second holder for a reagent vial; and*

*a heating element;*

*wherein the programmable controller is configured by software instructions to cause the pipetting device to transfer an aliquot of liquid from the reagent vial to the reaction vial when the reagent vial contains a solution comprising a hydrazine- or hydrazide-containing formaldehyde scavenger; proteinase K, EDTA, and a pH buffer, and*

*wherein the programmable controller is configured by software instructions to cause the heating element to heat the reaction vial to a temperature in the range of 80° C. to 100° C.*

*39. The system of claim 38, wherein the programmable controller is configured by software instructions to cause the heating element to heat the reaction vial for a time period of 15 minutes to 30 minutes.*

* * * * *